United States Patent [19]

Regnier et al.

[11] Patent Number: 4,824,836
[45] Date of Patent: Apr. 25, 1989

[54] SPIRO (4,5) DECONE COMPOUNDS

[75] Inventors: Gilbert Regnier, Chatenay Malabry; Claude Guillonneau, Clamart; Jacques Duhault, Croissy S/Seine; Michel Lonchampt, Rungis, all of France

[73] Assignee: Adir et Compagnie, Neuilly-sur-Seine, France

[21] Appl. No.: 196,303

[22] Filed: May 20, 1988

[30] Foreign Application Priority Data

May 22, 1987 [FR] France ................... 87 07186

[51] Int. Cl.$^4$ .................. A61K 31/445; C07D 498/10
[52] U.S. Cl. ........................... 514/278; 546/19
[58] Field of Search ................... 546/19; 514/278

[56] References Cited

U.S. PATENT DOCUMENTS 4,028,351 6/1977 Taccone ................... 546/19

Primary Examiner—Robert T. Bond
Attorney, Agent, or Firm—Gordon W. Hueschen

[57] ABSTRACT

Spiro (4,5) decane compounds of the formula:

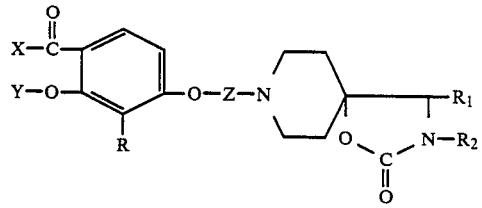

in which:
X is methyl and
Y is hydrogen or R'—CO— in which R' is $C_1$-$C_4$-alkyl or $C_1$-$C_4$-alkoxy,

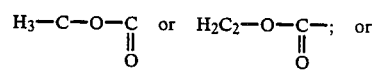

or X and Y together represent

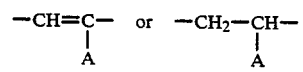

in each of which A is hydrogen, methyl, carboxy, methoxycarbonyl or ethoxycarbonyl;
R is $C_1$-$C_7$-alkyl optionally containing a double bond;
Z is a $C_2$-$C_7$-polymethylene chain optionally carrying an OH group;
$R_1$ is hydrogen or methyl; and
$R_2$ is hydrogen, R'—CO— or benzyloxycarbonyl;
and physiologically tolerable acid addition salts thereof.

These compounds may be used therapeutically especially in the treatment of asthma, allergic phenomena and bronchopathies.

9 Claims, No Drawings

SPIRO (4,5) DECONE COMPOUNDS

The present invention provides spiro(4,5)decane compounds of the general formula I:

$$\text{(I)}$$

[Structure: X-C(=O)- attached to benzene ring with Y-O- and R substituents, linked via -O-Z-N- to piperidine spiro-fused oxazolidinone bearing $R_1$ and $N-R_2$]

in which:

X represents a methyl radical; and
Y is selected from the group consisting of: a hydrogen atom, and a radical of the formula:

R'—CO— in which R' is selected from the group consisting of: alkyl and alkoxy radicals each containing from 1 to 4 carbon atoms, and (methyl and ethyl)-oxycarbonyl radicals, $(H_3C-O-\underset{\underset{O}{\|}}{C}-$ and $H_5C_2-O-\underset{\underset{O}{\|}}{C}-)$;

or X and Y together represent a chain selected from the group consisting of:
an ethenylene chain of the formula:

$-CH=\underset{\underset{A}{|}}{C}-$ and an ethylene chain of the formula:

$-CH_2-\underset{\underset{A}{|}}{CH}-$ in each of which A is selected from the group consisting of:
methyl radical and carboxy, methoxycarbonyl and ethoxycarbonyl groups;

R is selected from the group consisting of: ($C_1$ to $C_7$) straight-chain and branched alkyl radicals and these radicals containing a double bond;

Z is selected from the group consisting of: ($C_1$ to $C_7$) straight-chain and branched hydrocarbon chains, and hydroxyl ($C_1$ to $C_7$) straight hydrocarbon chains;

$R_1$ is selected from the group consisting of: a hydrogen atom and a methyl radical; and $R_2$ is selected from the group consisting of: a hydrogen atom, an acyl radical of the formula R'—CO— in which R' has the meaning defined above, and a benzyloxycarbonyl radical.

The prior art in this field is illustrated especially by French Pat. No. 1,441,575 and the corresponding BSM No. 4463M which each relate to spiro(4,5)decane compounds of the formula

[Structure: R-N piperidine spiro-fused to oxazolidinone with NH]

in which R represents, inter alia, the phenethyl and phenoxyethyl radicals, and to their use as medicaments having analgesic, anti-inflmmatory and broncholytic properties.

The compounds of the present invention differ from those of the prior art not only in their chemical structure but also in their pharmacological behaviour, as is demonstrated by the pharmaceutical study given as an example hereinafter.

The present invention also relates to a process for the preparation of the compounds of the general formula I, which process is based essentially on the reaction:

$$\text{(II)} + \text{HN-...} \rightarrow \text{(I)} + \text{H—Hal}$$

[Scheme: Compound II (aryl-O-Z-Hal) + Compound III (HN-piperidine-spiro-oxazolidinone with $R_1$, $N-R_2$) → (I) + H—Hal]

(Hal being a halogen atom, preferably a bromine atom). In general, the condensation of derivatives II and III is always carried out at a temperature of from 60° to 100° C., in a suitable solvent, such as acetonitrile or an aliphatic ketone containing 3 or 4 carbon atoms, in the presence of an agent that binds the hydracid formed in the course of the reaction. It is preferable to use as acceptor an excess of derivative III or, failing that, a tertiary base, such as triethylamine, or an alkaline carbonate, such as $K_2CO_3$ or $Na_2CO_3$.

This basic process has a certain number of variants according to the products to be prepared and, more precisely, according to the meanings of X, Y and $R_2$. All these variants are included in the present invention. Thus:

1. Where X represents a methyl radical:
    1.1. In order to obtain the compounds of the formula I in which Y and $R_2$ simultaneously represent a hydrogen atom, the compound of the general formula IIa:

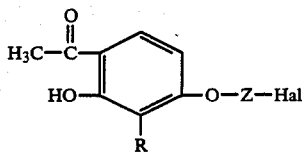
(IIa)

in which R, Z and Hal have the meanings given above, is condensed with a compound of the general formula IIIa

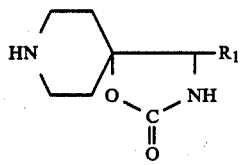
(IIIa)

in which $R_1$ has the meaning defined above, which results in the compounds of the general formula Ia

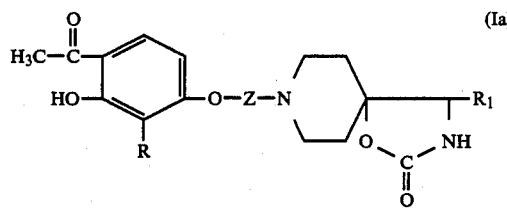
(Ia)

in which R, Z and $R_1$ have the meanings defined above.

1.2. In order to obtain the compounds I in acylated form at one or both of the sites Y and $R_2$, a compound of the general formula Ia is reacted with a reactive form of the acylating agent, such as, for example, an acid chloride R'COCl or an anhydride (R'COO)$_2$O, (R' in these formulae having the meaning defined above), taking into account the fact that the acylation is carried out first at the site $R_2$ and then at the site Y. Thus, by reacting a compound of the general formula Ia with the stoichiometric amount of acylating agent of the formula R'COCl or (R'COO)$_2$O, the diacylated form of the general formula Ib:

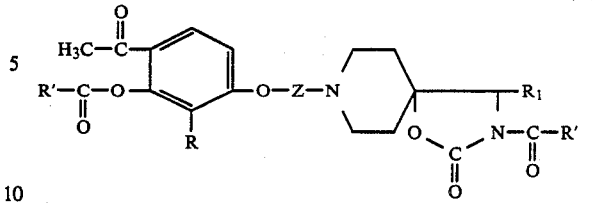
(Ib)

is obtained.

Such an acylation is carried out especially advantageously by effecting the reaction in the presence of a tertiary base, such as, for example, 4-dimethylaminopyridine, in a halogenated solvent, such as, for example, methylene chloride, at ambient temperature.

By reacting a compound of the general formula Ia with half the stoichiometric amount of the acylating agent of the formula R'COCl or (R'COO)$_2$O, there is obtained the form monoacylated at the site $R_2$ and having the general formula Ic:

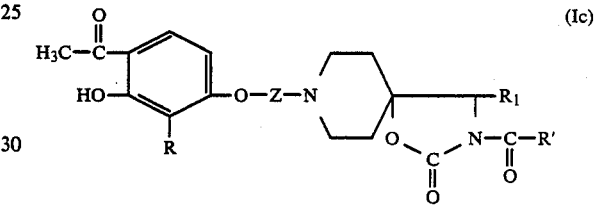
(Ic)

Finally, in order to obtain the form of the compounds I monoacylated exclusively at the site Y, the site $R_2$ is protected before carrying out the acylation and is then deprotected according to customary methods, that is to say: the compound of the formula

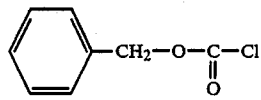

is reacted with the compound (Ia) in order to obtain the compound of the general formula Id:

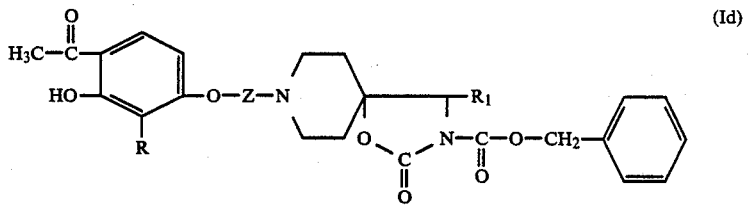
(Id)

in which R, Z and $R_1$ have the meanings defined above, which compound (Id) is acylated according to the method described above for the diacylation using R'COCl or (R'COO)$_2$O to obtain the compound of the general formula Ie:

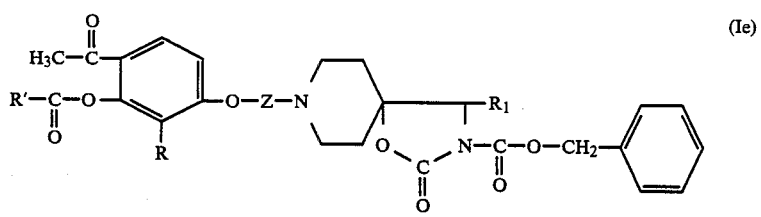

(Ie)

in which R, R', Z and R₁ have the meanings defined above, on which the deprotection of the site R₂ is carried out by hydrogenolysis of the benzyloxycarbonyl grouping to obtain a compound of the general formula If:

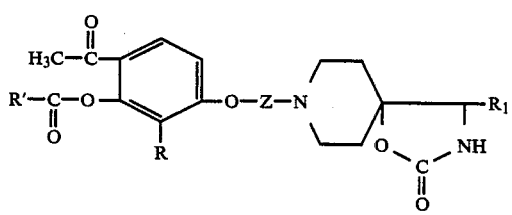

(If)

The hydrogenolysis of the benzyloxycarbonyl group of the compound (Ie) is advantageously carried out using hydrogen under normal pressure and in the presence of palladium/carbon as catalyst in a polar solvent, such as, for example, ethanol or methanol.

2. Where X and Y together represent an ethenylene or ethylene chain substituted by a carboxy group, it is expedient to condense the compound (III) with a methyl- or ethyl-esterified from of the corresponding compound (II) and then to hydrolyse the resulting compound using NaHCO₃ in order to free the carboxy function.

All the products of the general formula I are weak bases that can, as such, form salts with biologically compatible mineral or organic acids. These salts are also included in the present invention.

The products of the present invention can be purified by flash chromatography on a silica column (35–70μ) with CH₂Cl₂/CH₃OH systems, or by crystallisation in suitable solvents.

The starting materials used for the preparation of the derivatives of the present invention are either known products or products prepared according to a process known for the preparation of analogous compounds, as mentioned in the Table below:

| starting materials | preparation reference |
|---|---|
| CH₃CO–/HO–/–OH (R) | (R = allyl, n-propyl) W. BAKER and O. M. LOTHIAN J. Chem. Soc. (1935) 628–633 |
| CH₃OOC–...–OH (nC₃H₇) | R. A. APPLETON et al. J. Med. Chem. (1977) 20,371–378 |
| (chromanone with nC₃H₇, OH) | Analogous to D. HUCKLE et al. J. Med. Chem. (1969) 12,277 |
| (ketone with OCH₃, nC₃H₇) | Analogous to B. GRAFFE et al. J. Hetero Chem. (1975) 12,247–251 |
| HN–...–R₁ (piperidine oxazolidinone) | R₁ = H Science Union et Cie French Patent 1 441 575 R₁ = CH₃ J. MALLARD et al. Ch. therap. (1973) 393–397 |
| XCO–/YO–...–O–Z–Br (R) | Analogous to ELLI LILLY EP 0108592 A1 of 16th of May 1984 |

In the case of the starting materials of the general formula II in which Hal represents a bromine atom, the following products were prepared:

| R group structure | Z | m.p.* (Kofler) |
|---|---|---|
| XCO-O-C6H3(YO)(R) (general: X, Y on phenyl with R) | | |
| CH3O-, HO-, nC3H7- phenyl | —(CH2)2— | oil |
| CH3O-, HO-, nC3H7- phenyl | —(CH2)3— | oil |
| CH3O-, HO-, nC3H7- phenyl | —(CH2)4— | oil |
| CH3O-, HO-, nC3H7- phenyl | —(CH2)5— | oil |
| CH3O-, HO-, nC3H7- phenyl | —(CH2)6— | oil |
| CH3O-, HO-, nC3H7- phenyl | CH2—CHOH—CH2 | oil |
| CH3OOC-CH=C(O-)-CO- phenyl with nC3H7 | —(CH2)3— | 110° C. |
| chromanone with nC3H7 | —(CH2)3— | 64° C. |

-continued

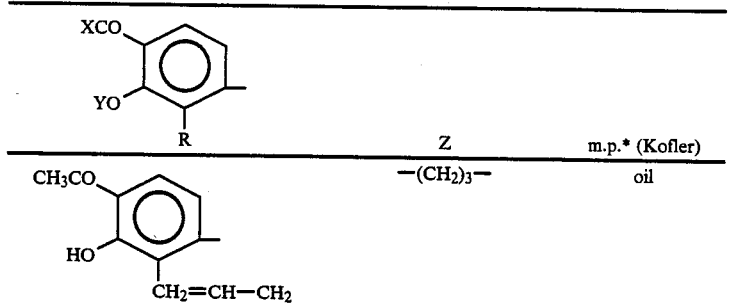

| | Z | m.p.* (Kofler) |
|---|---|---|
| CH₃CO-/HO-/CH₂=CH-CH₂ (R) | $-(CH_2)_3-$ | oil |

*all of these compounds were purified by flash chromatography on a SiO₂ column (35–70μ) with the system CH₂Cl₂/cyclohexane (50:50). The NMR spectra are in accordance with the proposed structures.

The compounds of the general formula I and their physiologically tolerable salts have valuable pharmacological and therapeutic properties, especially anti-bronchoconstrictive, anti-asthmatic, anti-allergic and anti-bronchoinflammatory properties, which therefore permit their use as medicaments, especially in the treatment of asthma and its long-term complications, in the prevention and treatment of allergic phenomena, especially early and late bronchoconstrictions, in the treatment of chronic obstructive bronchopathies, pulmonary arterial hypertension, respiratory symptoms of various diseases involving inflammation and oedema of the tracheobronchial tree and of the pulmonary interstice, and inflammatory affections of the upper respiratory passages.

The present invention relates to pharmaceutical compositions containing as active ingredient a compound of the general formula I or one of its physiologically tolerable salts mixed or associated with a suitable pharmaceutical excipient, such as, for example, distilled water, glucose, lactose, starch, talc, ethylcellulose, magnesium stearate or cocoa butter.

The pharmaceutical compositions so obtained are generally in dosage form and may contain from 20 to 80 mg of active ingredient. They may be, for example, in the form of tablets, dragées, soft gelatin capsules, suppositories, injectable or drinkable solutions and, depending on which form they take, they may be administered orally, rectally or parenterally at a dose of from 20 to 80 mg from 1 to 3 times per day.

The following Examples illustrate the invention, the melting points being determined using a capillary tube unless otherwise indicated.

EXAMPLE 1

8-[3-(2-propyl-3-hydroxy-4-acetylphenoxy)propyl]-1-oxa-2-oxo-3,8-diaza-spiro[4.5]decane

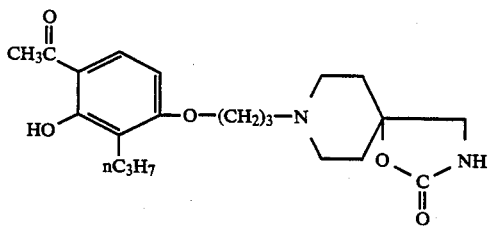

A solution containing 8 g (0.025 mol) of 4-(3-bromopropoxy)-3-n-propyl-2-hydroxyacetophenone (oil) and 7.9 g (0.05 mol) of 1-oxa-2-oxo-[8H]-3,8-diaza-spiro[4.5]decane is heated under reflux for 15 hours with 0.2 g of sodium iodide in 160 ml of acetonitrile. The solvent is then evaporated under reduced pressure and the residue is treated with 80 ml of water and 50 ml of CH₂Cl₂; the aqueous layer is decanted and the organic layer is washed with water and evaporated under reduced pressure. The semi-crystalline residue is purified by flash chromatography on a column containing 450 g of SiO₂ while eluting with the system CH₂Cl₂/CH₃OH (95:5) under a nitrogen pressure of 0.5 atmosphere. After evaporation of the eluates, 8.8 g of white crystals, melting at 112°–114° C., of 8-[3-(2-propyl-3-hydroxy-4-acetylphenoxy)propyl]-1-oxa-2-oxo-3,8-diaza-spiro[4.5]decane are obtained.

The following products were prepared in the same manner:

(a) 8-[2-(2-propyl-3-hydroxy-4-acetylphenoxy)ethyl]-1-oxa-2-oxo-3,8-diaza-spiro[4.5]decane, m.p. 128°–130° C.

(b) 8-[4-(2-propyl-3-hydroxy-4-acetylphenoxy)butyl]-1-oxa-2-oxo-3,8-diaza-spiro[4.5]decane, m.p. 112°–114° C.

(c) 8-[3-(2-propyl-3-hydroxy-4-acetylphenoxy)-2-hydroxypropyl]-1-oxa-2-oxo-3,8-diaza-spiro[4.5]decane, m.p. 145°–147° C.

(d) 8-[5-(2-propyl-3-hydroxy-4-acetylphenoxy)pentyl]-1-oxa-2-oxo-3,8-diaza-spiro[4.5]decane, m.p. 118°–120° C.

(e) 8-[6-(2-propyl-3-hydroxy-4-acetylphenoxy)hexyl]-1-oxa-2-oxo-3,8-diaza-spiro[4.5]decane, m.p. 136°–138° C.

(f) 8-[2-(2-propyl-3-hydroxy-4-acetylphenoxy)ethyl]-1-oxa-2-oxo-3,8-diaza-4-methyl-spiro[4.5]decane, m.p. 114°–116° C.

(g) 8-[3-(2-propyl-3-hydroxy-4-acetylphenoxy)propyl]-1-oxa-2-oxo-3,8-diaza-4-methyl-spiro[4.5]decane, m.p. 83°–85° C.

(h) 8-[3-(2-allyl-3-hydroxy-4-acetylphenoxy)propyl]-1-oxa-2-oxo-3,8-diaza-spiro[4.5]decane, m.p. 134°–136° C. (isopropanol).

(i) 8-[3-(2-ethoxycarbonyl-8-propyl-7-chrom-4-onyloxy)propyl]-1-oxa-2-oxo-3,8-diaza-spiro[4.5]decane, m.p. 152°–154° C.

(j) 8-[3-(4-oxo-7-propyl-7-chromanyloxy)propyl]-1-oxa-2-oxo-3,8-diaza-spiro[4.5]decane, m.p. 124°–126° C.

(k) 8-[3-(2-ethyl-3-hydroxy-4-acetylphenoxy)propyl]-1-oxa-2-oxo-3,8-diaza-spiro[4.5]decane, m.p. 150°–152° C. (isopropanol).

(l) 8-[3-(2-isobutyl-3-hydroxy-4-acetylphenoxy)propyl]-1-oxa-2-oxo-3,8-diaza-spiro[4.5]decane, m.p. 130°–132° C. (isopropanol).

EXAMPLE 2

8-[3-(2-propyl-3-hydroxy-4-acetylphenoxy)propyl]-1-oxa-2-oxo-3,8-diaza-4-methyl-spiro[4.5]decane

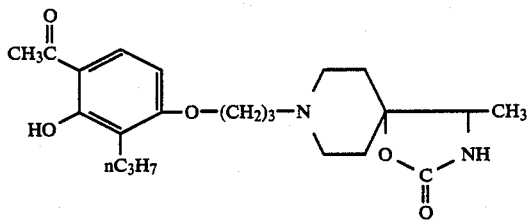

A solution of 8 g (0.025 mol) of 4-(3-bromopropoxy)-3-n-propyl-2-hydroxyacetophenone is heated for 15 hours under reflux with 4.25 g (0.025 mol) of 1-oxa-2-oxo-4-methyl-[8H]-3,8-diaza-spiro[4.5]decane in the presence of 3.45 g (0.025 mol) of $K_2CO_3$ and 0.2 g of sodium iodide. Then the same treatment as in Example 1 is carried out and 80 g of 8-[3-(2-propyl-3-hydroxy-4-acetylphenoxy)propyl]-1-oxa-2-oxo-3,8-diaza-4-methyl-spiro[4.5]decane are finally obtained in the form of white crystals melting at 83°–85° C. All the products of Examples 1 and 1a to 11 were prepared in the same manner.

EXAMPLE 3

8-[3-(2-carboxy-8-propyl-7-chrom-4-onyloxy)propyl]-1-oxa-2-oxo-3,8-diaza-spiro[4.5]decane

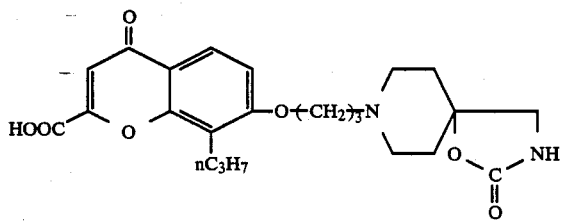

A solution of 7.1 g (0.015 mol) of 8-[3-(2-ethoxycarbonyl-8-propyl-7-chrom-4-onyloxy)propyl]-1-oxa-2-oxo-3,8-diaza-spiro[4.5]decane melting at 152°–154° C. and prepared in accordance with Example 1 is heated under reflux for 1 hr 30 min in 3500 ml of ethanol containing 6.3 g of $NaHCO_3$ dissolved in 35 ml of water. The solvent is then evaporated under reduced pressure and neutralised exactly by adding 75 ml of N NCl. Complete solubilisation takes place and this is followed by precipitation. The product is filtered and washed with water and ether. After drying, 6.5 g of white product are obtained. The product is taken up in 15 ml of water under reflux, and 30 ml of N HCl are added: complete dissolution takes place and this is followed by recrystallisation. The product is cooled, suction-filtered and dried in vacuo. 6 g of crystals of 8-[3-(2-carboxy-8-propyl-7-chrom-4-onyloxy)propyl]-1-oxa-2-oxo-3,8-diaza-spiro[4.5]decane hydrochloride melting at approximately 180°–200° C. with decomposition are finally obtained.

EXAMPLE 4

8-[3-(2-propyl-3-acetoxy-4-acetylphenoxy)propyl]-1-oxa-2-oxo-3,8-diaza-3-acetyl-spiro[4.5]decane

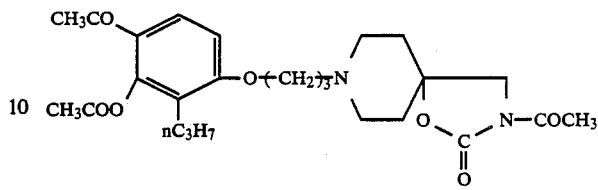

40 ml of acetic anhydride in solution in 100 ml of $CH_2Cl_2$ are added to a solution of 7.78 g (0.02 mol) of 8-[3-(2-propyl-3-hydroxy-4-acetylphenoxy)propyl]-1-oxa-2-oxo-3,8-diaza-spiro[4.5]decane, prepared in accordance with Example 1, in 100 ml of $CH_2Cl_2$ containing 5.4 g (0.044 mol) of 4-dimethylaminopyridine and then the solution is stirred for 4 hours at normal temperature. It is then evaporated to dryness and the residue is taken up in 50 ml of $CH_2Cl_2$ and 50 ml of 10% $NaHCO_3$. After decanting, the $CH_2Cl_2$ is dried over $Na_2SO_4$, the solution is evaporated and the residue is purified by flash chromatography on a column containing 450 g of $SiO_2$ under a nitrogen pressure of 0.5 atmosphere while eluting with the system $CH_2/CH_3OH$ (97:3). After evaporation of the eluates, 6.1 g of amorphous base are finally obtained which is converted into the fumarate in ethanol. 6.8 g of crystals of the acid fumarate of 8-[3-(2-propyl-3-acetoxy-4-acetylphenoxy)propyl]-1-oxa-2-oxo-3,8-diaza-3-acetyl-spiro[4.5]decane, melting at 144°–146° C., are isolated.

The following products were prepared in the same manner:

(a) 8-[3-(2-allyl-3-acetoxy-4-acetylphenoxy)propyl]-1-oxa-2-oxo-3,8-diaza-3-acetyl-spiro[4.5]decane, m.p. 130°–132° C.

(b) 8-[5-(2-propyl-3-acetoxy-4-acetylphenoxy)pentyl]-1-oxa-2-oxo-3,8-diaza-3-acetyl-spiro[4.5]decane, m.p. of the corresponding acid fumarate: 158A°–160° C. (isopropanol).

(c) 8-[3-(2-ethyl-3-acetoxy-4-acetylphenoxy)propyl]-1-oxa-2-oxo-3,8-diaza-3-acetyl-spiro[4.5]decane, m.p. 135°–136° C. (ethanol).

(d) 8-[3-(2-isobutyl-3-acetoxy-4-acetylphenoxy)propyl]-1-oxa-2-oxo-3,8-diaza-3-acetyl-spiro[4.5]decane, m.p. of the corresponding acid fumarate: 162°–164° C. (isopropanol).

EXAMPLE 5

8-[3-(2-allyl-3-hydroxy-4-acetylphenoxy)propyl]-1-oxa-2-oxo-3,8-diaza-3-acetyl-spiro[4.5]decane

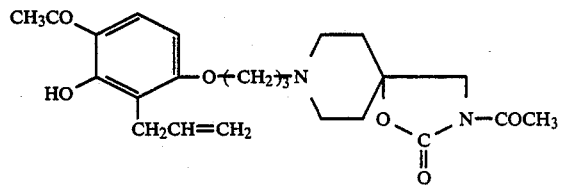

Proceeding in the same manner as in Example 4 and starting from 3.9 g (0.01 mol) of 8-[3-(2-allyl-3-hydroxy-4-acetylphenoxy)propyl]-1-oxa-2-oxo-3,8-diaza-spiro[4.5]decane, melting at 134°–136° C. and prepared in accordance with Example 1, and from 0.11 mol of acetic anhydride, 2.1 g of 8-[3-(2-allyl-3-hydroxy-4-acetylphenoxy)propyl]-1-oxa-2-oxo-3,8-diaza-3-acetyl-spiro[4.5]decane are finally obtained in the form of white crystals melting at 100°–102° C.

EXAMPLE 6

8-[3-(2-propyl-3-acetoxy-4-acetylphenoxy)propyl]-1-oxa-2-oxo-3,8-diaza-spiro[4.5]decane

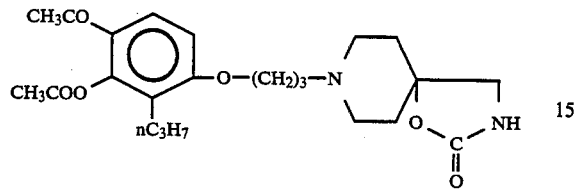

In accordance with Example 5, 8-[3-(2-propyl-3-hydroxy-4-acetylphenoxy)propyl]-1-oxa-2-oxo-3,8-diaza-3-benzyloxycarbonyl-spiro[4.5]decane, melting at 112° C., is first of all prepared with a yield of 50% starting from the compound described in Example 1 and from benzyl chloroformate.

The compound obtained is then converted in accordance with Example 4, with a yield of 87%, into 8-[3-(2-propyl-3-acetoxy-4-acetylphenoxy)propyl]-1-oxa-2-oxo-3,8-diaza-3-benzyloxycarbonyl-spiro[4.5]decane, which melts at 160°–162° C., using an excess of acetic anhydride in the presence of 4-dimethylaminopyridine. A solution of 9.2 g (0.016 mol) of the above compound in solution in 800 ml of 90% ethanol is hydrogenated under hydrogen (0.3 atmosphere) in the presence of 0.8 g of 5% Pd/C and 16.3 ml of N HCl. When the hydrogen has been completely absorbed, the catalyst is filtered off and evaporation to dryness is carried out. The crystalline residue is recrystallised from 300 ml of ethanol in the presence of 2 ml of ether, HCl (pH: 2). 6.7 g of 8-[3-(2-propyl-3-acetoxy-4-acetylphenoxy)propyl]-1-oxa-2-oxo-3,8-diaza-spiro[4.5]decane hydrochloride, melting at 233°–235° C., are recovered.

The following product was prepared in the same manner:

(a) 8-[5-(2-propyl-3-acetoxy-4-acetylphenoxy)pentyl]-1-oxa-2-oxo-3,8-diaza-spiro[4.5]decane, m.p. of the corresponding acid fumarate: 120°–122° C. (isopropanol).

EXAMPLE 7

Pharmacological study of the compounds of the invention

The compounds of the invention and fenspiride, a prior art product taken as reference substance, were subjected to the mastocyte degranulation test:

Peritoneal rat mastocytes are incubated in vitro in the presence of compound 48/80, which causes histamine granules to be released. The protective effect of the tested compounds is expressed in $IC_{50}$, that is to say the (molar) dose that inhibits this release by 50%.

The results obtained are set out in the following Table:

| Compounds of the Examples | Mastocyte degranulation in vitro - $IC_{50}$ (mole) |
| --- | --- |
| 1 | $2.4 \times 10^{-4}$ |
| 1a | $2 \times 10^{-4}$ |

-continued

| Compounds of the Examples | Mastocyte degranulation in vitro - $IC_{50}$ (mole) |
| --- | --- |
| 1b | $2 \times 10^{-4}$ |
| 1c | $10^{-3}$ |
| 1d | $1.1 \times 10^{-4}$ |
| 1e | $9.2 \times 10^{-5}$ |
| 1f | $10^{-4}$ |
| 1g | $2 \times 10^{-4}$ |
| 1h | $2.5 \times 10^{-4}$ |
| 1i | $10^{-4}$ |
| 1j | $10^{-4}$ |
| 1k | $8.3 \times 10^{-4}$ |
| 1l | $1.16 \times 10^{-4}$ |
| 2 | $2 \times 10^{-4}$ |
| 3 | $10^{-3}$ |
| 4 | $7.2 \times 10^{-4}$ |
| 4a | $2.5 \times 10^{-3}$ |
| 4b | $10^{-3}$ |
| 4c | $>10^{-3}$ |
| 4d | $7.3 \times 10^{-4}$ |
| 5 | $7.5 \times 10^{-4}$ |
| 6 | $1.2 \times 10^{-3}$ |
| 6a | $2 \times 10^{-3}$ |
| fenspiride | inactive |

A study of this Table demonstrates the superiority of the compounds of the present invention over the closest product of the prior art which itself is inactive in the mastocyte degranulation test.

In addition, the toxicity of the compounds of the present invention is low. The mean toxic dose determined in mice intraperitoneally with these compounds is of the same order or magnitude as that of fenspiride.

The low toxicity and the high activity of the present compounds therefore allow them to be used therapeutically, especially in the respiratory field.

We claim:

1. A compound selected from the group consisting of: spiro(4,5)decane compounds of the formula I:

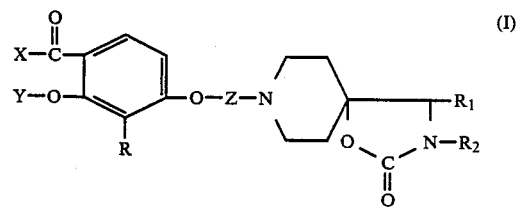

in which:

X represents a methyl radical; and

Y is selected from the group consisting of: hydrogen and a radical of the formula: R'—CO, in which R' is selected from the group consisting of ($C_1$ to $C_4$)alkyl, ($C_1$ to $C_4$)alkoxy, methyloxycarbonyl

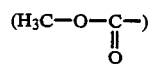

and ethyloxycarbonyl

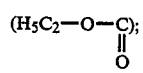

or X and Y together represent a chain selected from the group consisting of:

an ethenylene chain of the formula:

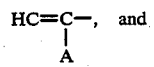

an ethylene chain of the formula:

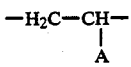

in each of which A is selected from the group consisting of: hydrogen, methyl, carboxy, methoxycarbonyl and ethoxycarbonyl;

R is selected from the group consisting of ($C_1$ to $C_7$) straight and branched chain alkyl and alkenyl radicals;

Z is selected from the group consisting of ($C_1$ to $C_7$) saturated and unsaturated straight and branched chain hydrocarbon radicals, and such hydroxy substituted radicals;

$R_1$ is selected from the group consisting of hydrogen and methyl; and $R_2$ is selected from the group consisting of: hydrogen, acyl of the formula: R'—CO— in which R' has the meaning defined above, and benzyloxycarbonyl; and physiologically tolerable acid addition salts thereof.

2. A compound of claim 1 which is:
8-[3-(2-propyl-3-hydroxy-4-acetylphenoxy)propyl]-1-oxa-2-oxo-3,8-diaza-spiro(4,5)decane.

3. A compound of claim 1 which is:
8-[5-(2-propyl-3-hydroxy-4-acetylphenoxy)pentyl]-1-oxa-2-oxo-3,8-diaza-spiro(4,5)decane.

4. A compound of claim 1 which is:
8-[6-(2-propyl-3-hydroxy-4-acetylphenoxy)hexyl]-1-oxa-2-oxo-3,8-diaza-spiro(4,5)decane.

5. A compound of claim 1 which is:
8-[3-(2-propyl-3-acetoxy-4-acetylphenoxy)propyl]-1-oxa-2-oxo-3,8-diaza-3-acetyl-spiro(4,5)decane.

6. A compound of claim 1 which is:
8-[3-(2-allyl-3-acetoxy-4-acetylphenoxy)propyl]-1-oxa-2-oxo-3,8-diaza-3-acetyl-spiro(4,5)decane.

7. A compound of claim 1 which is:
8-[3-(2-propyl-3-acetoxy-4-acetylphenoxy)propyl]-1-oxa-2-oxo-3,8-diaza-spiro(4,5)decane.

8. Pharmaceutical compositions, useful in the treatment of asthma, allergic phenomena, a chronic obstructive bronchiopathy, pulmonary arterial hypertension, or an inflammatory affection of the upper respiratory passages, containing as active ingredient an amount of a compound of claim 1 which is effective for such purpose together with a pharmaceutically-acceptable pharmaceutical carrier.

9. A method for treating a living animal body afflicted with asthma, allergic phenomena, a chronic obstructive bronchopathy, pulmonary arterial hypertension, or an inflammatory affection of the upper respiratory passages, comprising the step of administering to the said living animal an amount of a compound of claim 1 which is effective for the alleviation of the said condition.

* * * * *

UNITED STATES PATENT AND TRADEMARK OFFICE
CERTIFICATE OF CORRECTION

PATENT NO. : 4,824,836

DATED : April 25, 1989

INVENTOR(S) : Gilbert Regnier, Claude Guillonneau, Jacques Duhault and Michel Lonchampt It is certified that error appears in the above-identified patent and that said Letters Patent is hereby corrected as shown below:

```
Title Page, [54], in the title; "DECONE" should read -- DECANE --

Col. 1, line 2; "DECONE" should read -- DECANE --
Col. 2, line 22; "inflmmatory" should read -- inflammatory --
Col. 5, line 43; "from" should read -- form --
Col. 11, line 54; "NCl" should read -- HCl --
Col. 12, line 42; "158A°-160°" should read -- 158°-160° --
Col. 14, line 32; "or" should read -- of --
```

Signed and Sealed this

Seventeenth Day of April, 1990

Attest:

HARRY F. MANBECK, JR.

Attesting Officer

Commissioner of Patents and Trademarks